US010045882B2

(12) United States Patent
Balicki et al.

(10) Patent No.: US 10,045,882 B2
(45) Date of Patent: Aug. 14, 2018

(54) SURGICAL INSTRUMENT AND SYSTEMS WITH INTEGRATED OPTICAL SENSOR

(75) Inventors: Marcin A. Balicki, Baltimore, MD (US); Russell H. Taylor, Severna Park, MD (US); Jin U. Kang, Ellicott City, MD (US); Peter L. Gehlbach, Hunt Valley, MD (US); James T. Handa, Baltimore, MD (US); Jaeho Han, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 784 days.

(21) Appl. No.: 12/917,168

(22) Filed: Nov. 1, 2010

(65) Prior Publication Data

US 2011/0106102 A1   May 5, 2011

Related U.S. Application Data

(60) Provisional application No. 61/256,560, filed on Oct. 30, 2009.

(51) Int. Cl.
*A61F 9/00* (2006.01)
*A61F 9/007* (2006.01)
*A61B 3/10* (2006.01)
*A61B 3/12* (2006.01)
*A61B 34/00* (2016.01)
*A61B 90/00* (2016.01)
*A61B 34/30* (2016.01)

(52) U.S. Cl.
CPC .......... *A61F 9/00727* (2013.01); *A61B 3/102* (2013.01); *A61B 3/1005* (2013.01); *A61B 3/1225* (2013.01); *A61B 34/75* (2016.02); *A61B 34/76* (2016.02); *A61B 34/30* (2016.02); *A61B 90/361* (2016.02); *A61B 2090/061* (2016.02); *A61B 2090/3735* (2016.02)

(58) Field of Classification Search
CPC ........ A61B 19/5212; A61B 2019/2292; A61B 2019/5234; A61B 3/1005; A61B 3/102
USPC .......................... 606/130, 161, 166, 167, 170
See application file for complete search history.

(56) References Cited

U.S. PATENT DOCUMENTS 5,554,155 A * 9/1996 Awh et al. ...................... 606/16
6,004,314 A   12/1999 Wei et al.
6,445,939 B1  9/2002 Swanson et al.
(Continued)

OTHER PUBLICATIONS

Sjaarda R.N., Michels R.G., Macular pucker. In: SJ Ryan, Editor, Retina. vol. 3. (2nd ed), Mosby, St. Louis. pp. 2301-2312. (1994).
(Continued)

*Primary Examiner* — Gregory Anderson
*Assistant Examiner* — Sarah Simpson
(74) *Attorney, Agent, or Firm* — Venable, LLP; Henry J. Daley

(57) ABSTRACT

A surgical instrument has a surgical tool that has a proximal end and a distal end, and an optical sensor that has at least a portion attached to the surgical tool. The surgical tool has a portion that is suitable to provide a reference portion of the surgical tool, and the optical sensor has an end fixed relative to the reference portion of the surgical tool such that the reference portion of the surgical tool can be detected along with tissue that is proximate or in contact with the distal end of the surgical tool while in use.

22 Claims, 6 Drawing Sheets

(56) References Cited

U.S. PATENT DOCUMENTS

| | | | |
|---|---|---|---|
| 6,485,413 | B1 | 11/2002 | Boppart et al. |
| 6,564,087 | B1 | 5/2003 | Pitris et al. |
| 6,599,247 | B1 | 7/2003 | Stetten |
| 6,718,196 | B1 | 4/2004 | Mah et al. |
| 6,975,898 | B2 | 12/2005 | Seibel |
| 7,016,048 | B2 | 3/2006 | Chen et al. |
| 7,126,303 | B2 | 10/2006 | Farritor et al. |
| 7,261,687 | B2 | 8/2007 | Yang |
| 7,930,065 | B2 | 4/2011 | Larkin et al. |
| 8,622,935 | B1 | 1/2014 | Leo |
| 2003/0144594 | A1* | 7/2003 | Gellman ............... A61B 1/015 600/466 |
| 2005/0027199 | A1 | 2/2005 | Clarke |
| 2005/0228270 | A1* | 10/2005 | Lloyd et al. ............ 600/424 |
| 2006/0142657 | A1* | 6/2006 | Quaid et al. ............ 600/424 |
| 2008/0058629 | A1* | 3/2008 | Seibel ................ A61B 1/0008 600/368 |
| 2008/0218770 | A1 | 9/2008 | Moll et al. |
| 2008/0319464 | A1* | 12/2008 | Bischoff et al. ............ 606/166 |
| 2009/0048611 | A1* | 2/2009 | Funda et al. ............ 606/130 |

OTHER PUBLICATIONS

Xuan Liu, Xiaolu Li, Do-Hyun Kim, Ilko Ilev and Jin U. Kang, "Fiber Optic Fourier-domain Common-path OCT," C. Optics Letters, vol. 06, Issue 12, pp. 899-903, (2008).

Mitchell, B., Koo, J., Iordachita, I., Kazanzides, P., Kapoor, A.,Handa, J., Hager, G., Taylor, R.: Development and Application of a New Steady-Hand Manipulator for Retinal Surgery. IEEE ICRA, 623-629 (2007).

Riviere, W. Ang, and P. Khosla, "Toward active tremor canceling in handheld microsurgi-cal instruments," IEEE Trans Rob Autom, vol. 19, pp. 793-800, (2003).

Kapoor A., Deguet A., Kazanzides P., Software components and frameworks for medical robot control. IEEE ICRA, pp. 3813-3818, (2006).

Fujimoto J. G., Pitris C., Boppart S.A.; Brezinski M.E., Optical coherence tomography: an emerging technology for biomedical imaging and optical biopsy. Neoplasia 2( 1-2): 9-25, (2000).

Herrmann J. M., Boppart S. A., Bouma B. E., Tearney G. J., Pitris C., Brezinski M. E., Fujimoto J.G., Real time imaging of laser intervention with optical coherence tomography, in Biomedical Optical Spectroscopy and Diagnostics / Therapeutic Laser Applications. vol. 22 of OSA Trends in Optics and Photonics Series, paper TSuD2, (1998).

Boppart S.A., Nguyen F.T., Zysk A.M., Chaney E.J., Kotynek J.G., Oliphant U.J., Bellafiore F.J., Rowland K.M., Johnson P.A., Coherent optical imaging and guided interventions in breast cancer: translating technology into clinical applications. Proc. SPIE 6991, 699102 ,(2008).

Han S., Sarunic M.V.., Wu J., Humayun M., Yang C, Handheld forward-imaging needle endoscope for ophthalmic optical coherence tomography inspection. J. Biomed. Opt. 13, 020505, (2008).

* cited by examiner

SURGICAL INSTRUMENT AND SYSTEMS WITH INTEGRATED OPTICAL SENSOR

CROSS-REFERENCE OF RELATED APPLICATION

This application claims priority to U.S. Provisional Application No. 61/256,560 filed Oct. 30, 2009, the entire contents of which are hereby incorporated by reference.

This invention was made with government support under 1R01 EB 007969-01 awarded by the Department of Health and Human Services, National Institutes of Health. The government has certain rights in the invention.

BACKGROUND

1. Field of Invention

The field of the currently claimed embodiments of this invention relates to surgical instruments and systems that incorporate the surgical instruments, and more particularly to systems and surgical instruments that have integrated optical sensors.

2. Discussion of Related Art

Vitreoretinal surgery addresses prevalent sight-threatening conditions such as retinal detachment, macular pucker, macular holes, and vision threatening conditions in which epiretinal scar tissue is removed. The technical demands placed on the surgeon by these procedures are extreme. In current practice, retinal surgery is performed under an operating microscope with free-hand instrumentation. Human limitations include an inability to clearly visualize surgical targets, physiological hand tremor, and lack of tactile feedback in tool-to-tissue interactions. In addition, tool limitations, such as lack of proximity sensing or smart functions, are important factors that contribute to surgical risk and reduce the likelihood of achieving surgical goals. Current instruments do not provide physiological or even basic interpretive information, e.g. the distance of the instrument from the retinal surface, the depth of instrument penetration into the retina or an indication of the force exerted by the instrument on the retinal tissues. Surgical outcomes (both success and failure) are limited, in part, by technical hurdles that cannot be overcome by current instrumentation. For example, in the most technically demanding cases, there may not be a set of tools that allows the "typical" retina surgeon to remove sufficient epiretinal scar tissue to assure surgical success.

Peeling of epiretinal membranes (ERMs) from the surface of the retina is one example where there is a need for improved surgical instruments and systems. ERM peeling is a common and extremely demanding surgical procedure. ERMs are scar tissue that form on the surface of the retina, contract, and compromise retinal function. ERMs are present in 2-6.4% of people (Sjaarda R. N., Michels R. G., Macular pucker. In: S J Ryan, Editor, Retina. Vol. 3. (2nd ed), Mosby, St. Louis. pp. 2301-2312. (1994)). Visual dysfunction resulting from ERMs includes: blurred vision, image distortion, and altered image size. Surgical removal of an ERM involves identifying or creating an "edge" that is then grasped and peeled. Some ERMs provide clear visual evidence of edges that may be grasped. Others require creation of an edge by the surgeon. This may be performed by incising the membrane surface, by bluntly creating an edge, or by gently grasping the membrane with a forceps and creating a tear in the ERM. Each of these maneuvers requires excellent visualization, high levels of manual dexterity and micro-instrumentation. Furthermore, this procedure is performed with a comparatively large metal instrument without tactile sensation. During this time, a patient's involuntary and voluntary movement must be manually compensated by the surgeon while the instrument is in direct contact with fragile intraocular tissue. Incorrect micron-magnitude movements can cause retinal tears, retinal detachment, visual field defects, retinal hemorrhage, local retinal edema, nerve fiber layer injury, and macular holes, all of which can contribute to blindness.

Optical coherence tomography (OCT) provides very high resolution (micron scale) images of anatomical structures within the retina. Within Ophthalmology, OCT systems typically perform imaging through microscope optics to provide 2D cross-sectional images ("B-mode") of the retina. These systems are predominantly used for diagnosis, treatment planning, and, in a few cases, for optical biopsy and image guided laser surgery.

ERMs are recognized by Optical Coherence Tomography (OCT) as thin, highly reflective bands anterior to the retina. A potential dissection plane between the ERM and the retina is usually clearly visible in the scan, but is invisible to the surgeon through an operating microscope, even with very high magnification. In other work, our laboratory has explored registration of preoperative OCT images to intra-operative microscope images to aid in identifying ERM edges for initiating ERM removal. However, epiretinal membranes can grow and further distort retinal architecture. It is therefore, unclear whether preoperative images would provide a useful guide if the interval between the preoperative image acquisition and surgery allows for advancement of the ERM.

There thus remains the need for improved instruments and systems for precision manipulation of objects, such as, but not limited to, microsurgical applications.

SUMMARY

A surgical system according to some embodiments of the current invention has a surgical instrument, a data processor in communication with the optical instrument, and a information output system in communication with the data processor and arranged to display information to a surgeon during a surgical procedure. The surgical instrument includes a surgical tool having a proximal end and a distal end, and an optical sensor having at least a portion attached to the surgical tool. The surgical tool has a portion that is suitable to provide a reference portion of the surgical tool, and the optical sensor has an end fixed relative to the reference portion of the surgical tool such that the reference portion of the surgical tool can be detected along with tissue that is proximate or in contact with the distal end of the surgical tool while in use.

A surgical instrument according to some embodiments of the current invention has a surgical tool that has a proximal end and a distal end, and an optical sensor that has at least a portion attached to the surgical tool. The surgical tool has a portion that is suitable to provide a reference portion of the surgical tool, and the optical sensor has an end fixed relative to the reference portion of the surgical tool such that the reference portion of the surgical tool can be detected along with tissue that is proximate or in contact with the distal end of the surgical tool while in use.

A method of performing precision manipulations of an object according to some embodiments of the current invention includes providing an instrument that has a tool and an optical sensor having at least a portion attached to the tool; optically observing a reference point on the tool in conjunction with an object to be manipulated; determining a relative position of the reference point on the tool and a selected portion of the object; and conveying the relative position information to a user of the instrument.

BRIEF DESCRIPTION OF THE DRAWINGS

Further objectives and advantages will become apparent from a consideration of the description, drawings, and examples.

DETAILED DESCRIPTION

Figure 1:
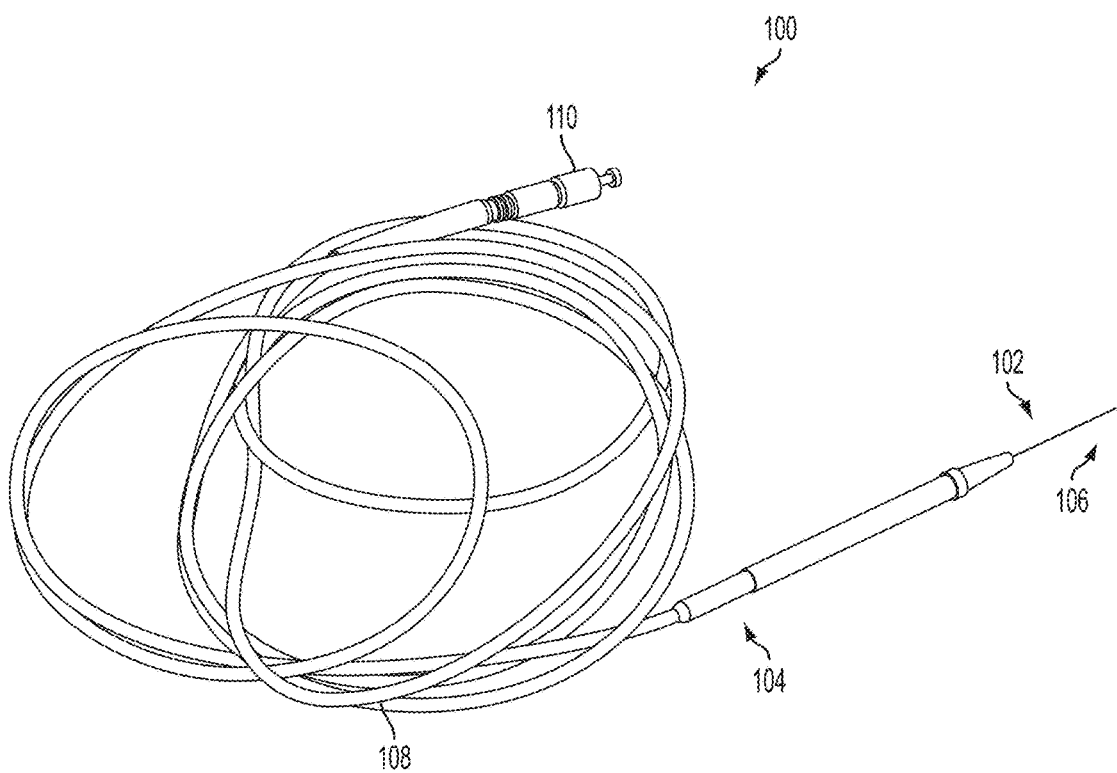
FIG. 1 shows an embodiment of a surgical instrument according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of the current invention are directed to a new class of microsurgical instruments incorporating common path optical coherence tomography (CP-OCT) capabilities. For example, direct imaging of the ERM relative to the surgeon's instruments would be very useful either as a replacement for or supplement to the preoperative OCT images. According to an embodiment of the current invention, direct imaging of the local anatomy relative to the instruments can be used to provide feedback on tool-to-tissue distances and real-time updates during tissue dissection. These instruments may be used freehand or with robotic assistance. An example prototype uses a 25 gauge microsurgical pick that incorporates a single 125 µm diameter optical fiber interfaced to a Fourier Domain CP-OCT system developed in our laboratory. It provides end point sensing at the surgical site allowing for real time feedback of tool location and tissue characteristics to the surgeon via a visual display, tactile display, robotic assistance or auditory feedback. This information can be used with a robotic assistant in a number of ways.

The following are three examples of capabilities that have been demonstrated on simple phantom models simulating vitreoretinal surgery according to an embodiment of the current invention:

1) enforcement of safety constraints preventing unintentional collisions of the instrument with the retinal surface;

2) the ability to scan the instrument across a surface while maintaining a constant distance offset; and 3) the ability to place the instrument over a subsurface target identified in a scan and then penetrate the surface to hit the target.

Instruments according to some embodiments of the current invention can allow for simultaneous imaging and surgical intervention functionality integrated into a single instrument. Registration of the instrument to the optical sensor is achieved by a reference portion of the instrument that is visible in the field of view of the optical sensor according to an embodiment of the current invention. Furthermore, multiple imaging probes can be integrated into the instrument for increased imaging volume, multiple imaging directions, increased resolution, or provide other types of imaging for simultaneous multimodal imaging functionality according to other embodiments of the current invention. Multiple imaging point probes (multi core fiber, or multifiber bundle) can improve the registration of the tool tip to optical sensor in some embodiments.

A surgical instrument 100 according to an embodiment of the current invention is shown in FIG. 1. The surgical instrument 100 includes a surgical tool 102 having a proximal end 104 and a distal end 106, and an optical sensor having at least a portion attached to the surgical tool 102. In FIG. 1, an optical fiber that is not directly visible runs along a lumen within the surgical tool 102 and is attached to the surgical tool 102. The optical fiber is enclosed within a protective cable 108, which has a standard fiber coupler 110 in this example. As one can see more clearly in FIG. 2, the surgical tool 102 has a portion that is suitable to provide a reference portion 112 of the surgical tool 102. The optical sensor 114 (see FIG. 3) has an end 116 fixed relative to the reference portion 112 of the surgical tool 102 such that the reference portion 112 of the surgical tool 102 can be detected along with tissue 118 that is proximate or in contact with the distal end 106 of the surgical tool 102 while in use.

Figure 2:
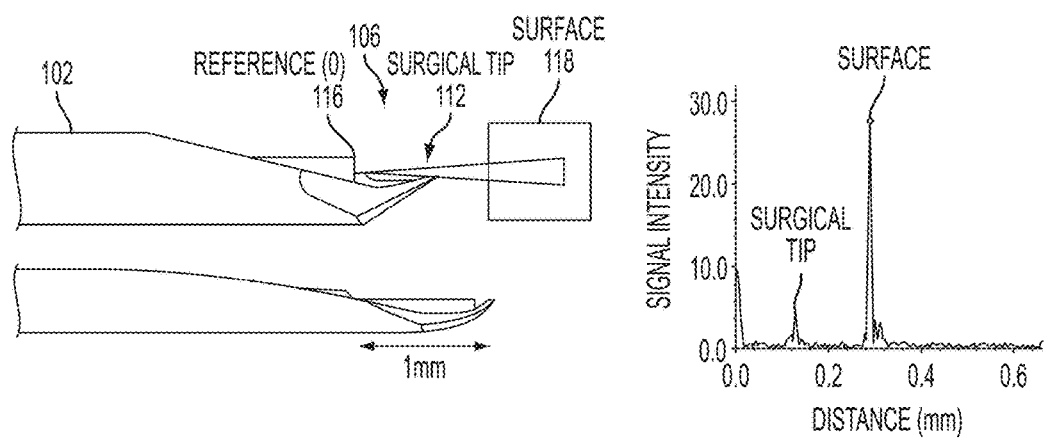
FIG. 2 shows a CAD side view of microsurgical pick with integrated fiber optic OCT probe according to an embodiment of the current invention (Top Left); a photograph of an actual prototype (Bottom Left); and A-Scan data of a sample using the prototype (Right).
Figure 3:
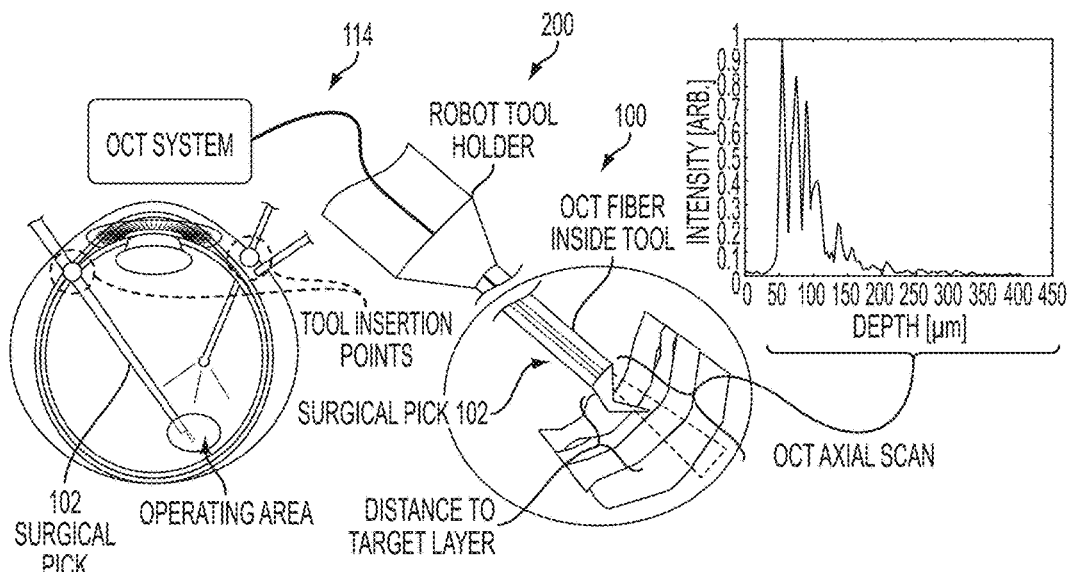
FIG. 3 provides a schematic illustration on the left of a surgical system according to an embodiment of the current invention. The right-hand side shows axial OCT scan data.
Figure 4:
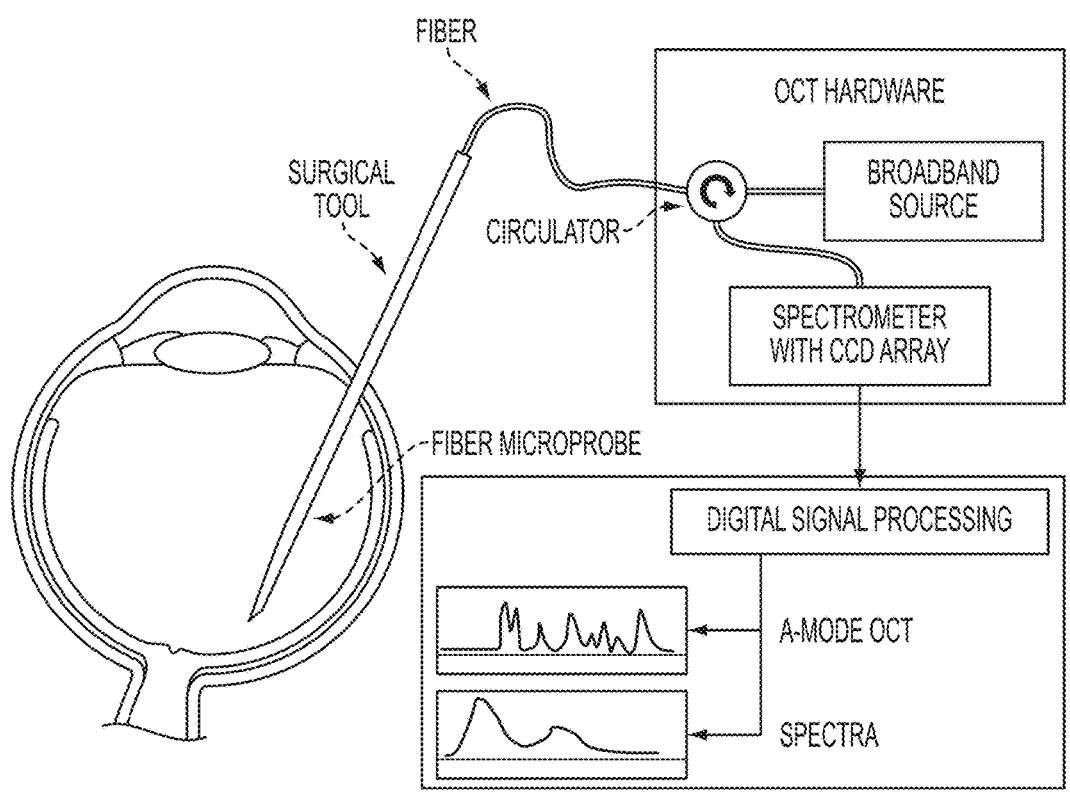
FIG. 4 is a schematic illustration of a surgical instrument according to an embodiment of the current invention.

In the example of FIG. 1, the surgical instrument 100 is shown with a portion of the optical sensor which can be connected through fiber coupler 110 to the remaining portion of the optical sensor. In the example of FIG. 3, the optical sensor 114 is an optical coherence tomography (OCT) system. In other embodiments, one could include more than one OCT or other type of optical sensor into the surgical instrument 100 within broad concepts of the current invention. In addition, although it can be advantageous for many applications to provide much of the optical sensor 114 external to the tool as is shown in the examples of FIGS. 1-3, the broad concepts of the current invention also include embodiments in which the entire sensor or sensors are included within the surgical tool. The optical coherence tomography system in the embodiment of FIG. 3 includes a single-mode optical fiber that provides the fixed end 116 of the optical sensor 114, the single-mode optical fiber being arranged to direct light to both the reference portion 112 of the surgical tool 102 and the tissue 118 proximate or in contact with the distal end 106 of the surgical tool 102 and to detect light reflected back from both the reference portion 112 of the surgical tool 102 and the tissue 118 to provide information regarding a relative distance of the distal end 106 of the surgical tool 102 to selected portions of the tissue 118. The term "reflected back" is intended to have a broad meaning to include both specular reflection as well as scattering, etc., as long as the light is reflected back. In addition, the term "light" is intended to have a broad meaning to include both visible light and light that is not visible to humans, such as infrared (IR) and ultraviolet light. In some embodiments of the current invention, the OCT system can make use of IR sources to provide significantly greater penetration depths into tissue than visible light, for example. Some embodiments of the current invention can include a broad band source in the OCT system, for example (see FIG. 4). However, the general concepts of the current invention are not limited to the particular types of light sources used in the optical sensor 114. Frequency domain OCT detection systems have been found to be suitable for some particular applications of the current invention; however, the general concepts of the current invention do not exclude the use of time domain OCT systems. Furthermore, some embodiments of the optical sensor can be without light sources, depending instead on ambient or external light sources.

Alternatively, or in addition to the OCT system illustrated as the optical sensor 114, the optical sensor 114 could be or include an optical imaging system. For example, the optical imaging system could include an optical fiber, or a bundle of optical fibers to simultaneously image the reference portion 112 of the surgical tool 102 and the tissue 118 proximate or in contact with the distal end 106 of the surgical tool 102. In some embodiments, the surgical tool 102 can be a pick, for example, that is suitable for use in eye surgery. However, the general concepts of the current invention are not limited to the particular type of surgical tool. One can imagine a vast range of types of surgical tools that are suitable for surgical tool 102, such as, but not limited to picks, tweezers, knives, light delivery devices, scissors, injectors, fragmenters, spatulas, peeling tools, vitrectomy tools, or other microsurgery tools. The surgical instrument can be adapted to integrate into a robotic system, such as is, illustrated by surgical system 200 in FIG. 3 or the hand-held robot 300 shown in FIG. 5.

Figure 5:
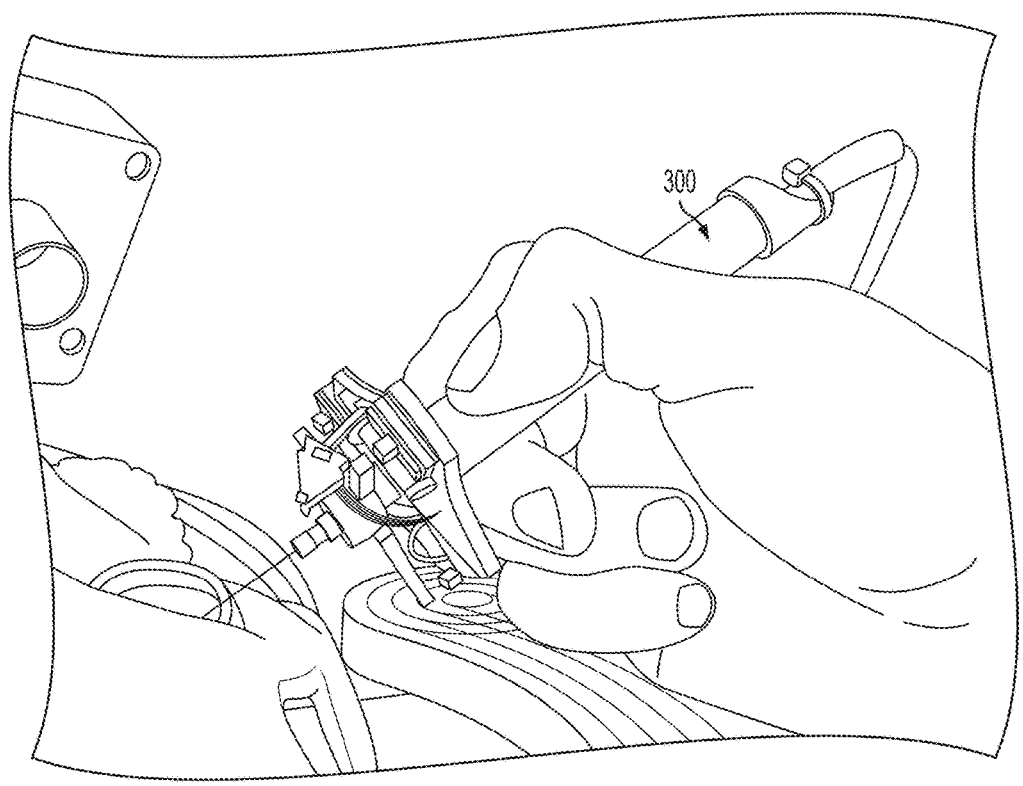
FIG. 5 shows a surgical system including a surgical instrument and a hand-held robot according to an embodiment of the current invention.
Figure 6:
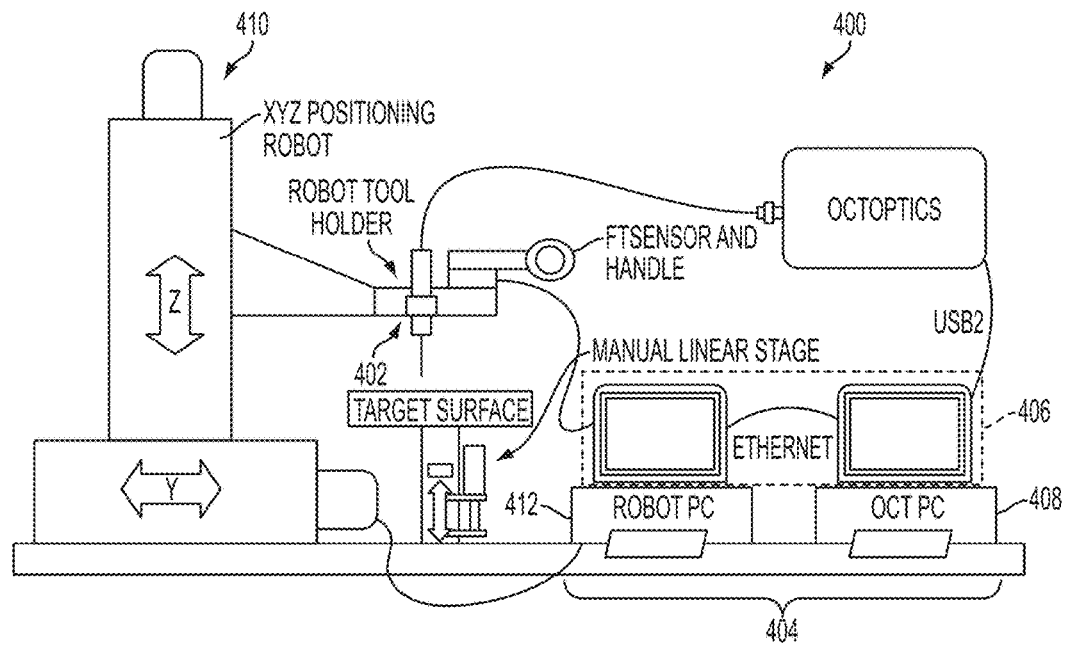
FIG. 6 is a schematic illustration of a surgical system according to an embodiment of the current invention.

FIG. 5 is a schematic illustration of a surgical system 400 according to an embodiment of the current invention. The surgical system 400 includes a surgical instrument 402, a data processor 404 in communication with the surgical instrument 402, and an information output system 406 in communication with the data processor 404 and arranged to display information to a surgeon during a surgical procedure. According to some embodiments of the current invention, the surgical instrument 402 can be surgical instrument 100 as described above, for example. In the example of FIG. 6, the surgical instrument 402 has a dedicated data processor, such as OCT PC 408. However, the broad concepts of the current invention are not limited to only the particular architecture shown in FIG. 6. For example data processor could perform the processing for the OCT system as well as for other portions of the surgical system 400. The surgical system 400 also includes a robotic system 410. The robotic system 410 can have a dedicated data processor 412, for example, or it could be included on a single multipurpose processor along with the OCT processor, for example. The data processor 404 should be considered generally to cover one or more data processor, including one or more remote processors. The surgical system 400 illustrates video displays as an example of information output system 406. However, the general concepts of the current invention are not limited to this particular example. The information output system could be, or include, head mounted displays, haptic or audio devices that serve the function of conveying information, and/or means of providing information to the surgeon. The robotic system 400 can be, but is not limited to, a steady-hand robotic system or a hand-held robotic system, for example. A hand-held robotic system that has been found to be suitable for some applications is the CMU Micron robot. However, the broad concepts of the current invention are not limited to this particular example. In some embodiments of the current invention, the data processor 404 can be configured to provide at least one of a warning signal or a feedback response signal based on a value of a relative position of the distal end of the surgical instrument to the tissue. In some embodiments of the current invention, the data processor 404 can be configured to provide a feedback response signal to the robotic system based on a value of at least one of a relative distance of the distal end of the surgical instrument from the tissue or a position of the instrument such that the robotic system provides a feedback response.

In some embodiments of the current invention, the data processor can be configured to perform one or more of the above-noted functions, i.e., 1) enforcement of safety constraints preventing unintentional collisions of the instrument with the retinal surface; 2) the ability to scan the instrument across a surface while maintaining a constant distance offset; and/or 3) the ability to place the instrument over a subsurface target identified in a scan and then penetrate the surface to hit the target.

EXAMPLES

The following provides some examples according to some embodiments of the current invention. These examples are provide to facilitate a description of some of the concepts of the invention and are not intended to limit the broad concepts of the invention.

Materials

OCT Integrated Pick Instrument:

Vitreoretinal picks are commercially available in a variety of sizes with the most commonly used ranging from 25-20 gauge (0.5 mm to 0.9 mm diameter). Sharp picks are used to incise taut surface membranes and engage and elevate membrane edges for ERM peeling. The simplicity of this basic tool permits the surgeon to quickly craft a sharp edged pick from an appropriately sized surgical needle by bending the beveled tip with a needle holder. The surgeon co-inventors routinely use this method to create such picks.

For our experiments, we have adapted this method to permit incorporation of a single fiber OCT probe to enable simultaneous A-mode imaging and tissue manipulation. Our prototype picks were constructed from 25 gauge, 38 mm surgical needles with 0.24 mm ID and 0.5 mm OD. We bent the beveled point approximately 200-300 μm from the tip so that the tip intersected with the central axis of the needle lumen. A cleaved optical fiber stripped to glass cladding was inserted through the lumen, bonded in place so that the cleaved end is approximately 135 μm from the tip, while the other end is interfaced to the CP-OCT system. The tip is visible in the OCT A-mode image, thus providing a reference point for the relative distance of the tool to tissue being scanned (see FIG. 2).

Figure 8:
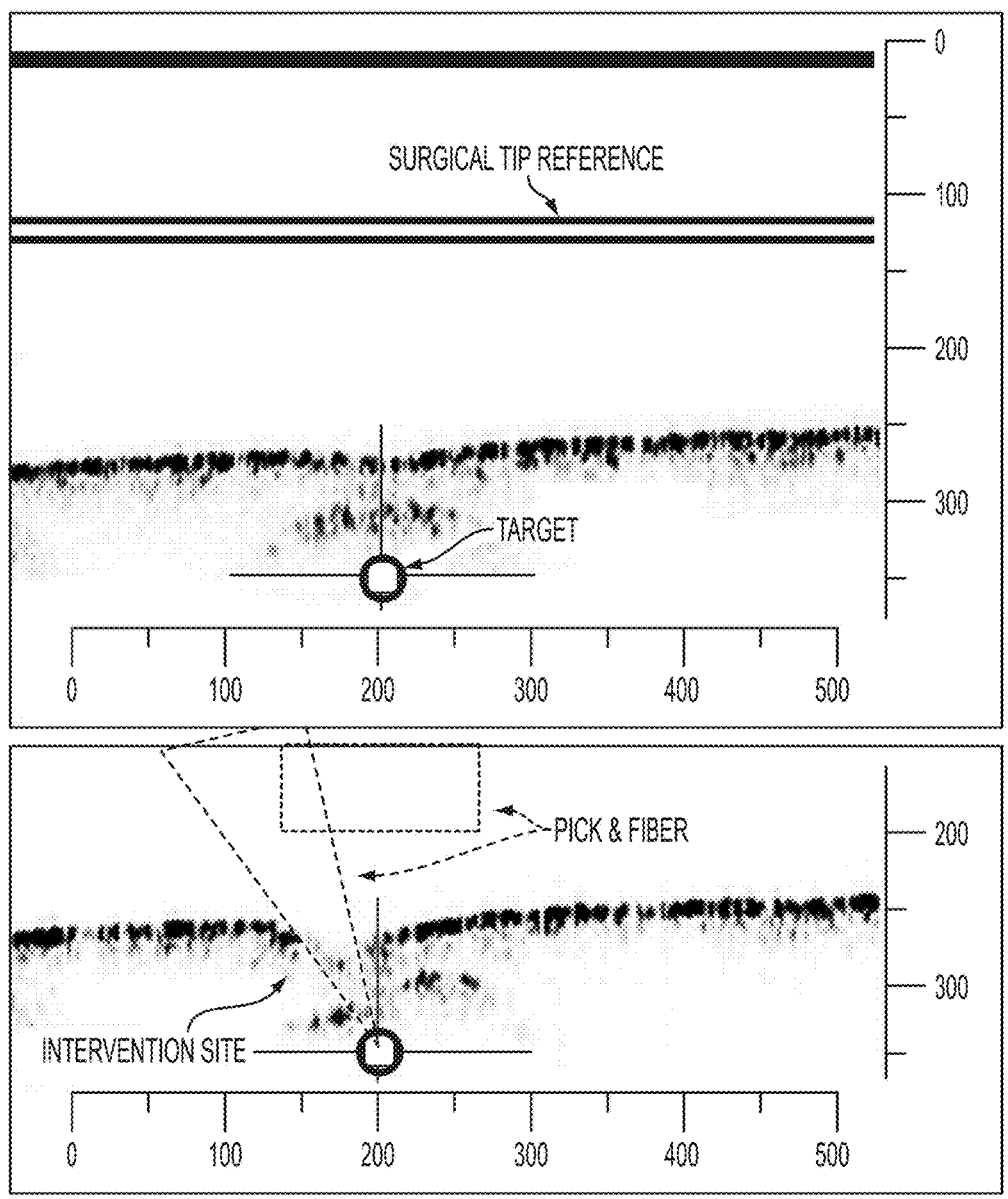
FIG. 8 is a B-Mode scan before and after intervention for a surgical system according to an embodiment of the current invention.

Optical Coherence Tomography System:

The optical fiber from the tool is integrated with a common path Fourier domain OCT system developed in our laboratory (see Xuan Liu, Xiaolu Li, Do-Hyun Kim, Ilko Ilev and Jin U. Kang, "Fiber Optic Fourier-domain Common-path OCT," C. Optics Letters, Vol. 06, Issue 12, pp. 899-903, 2008). It is the simplest, most compact imaging technique of its kind. This system is robust, inexpensive, and can utilize simple interchangeable probes. Our system uses an SLED light source centered near 0.8-μm wavelength with a fiber optic directional 2×2 coupler, and a USB spectrometer (HR4000, Ocean Optics Inc.). The optical fiber probes presented here are a single mode fiber (NA 0.14) with ~9 μm core size, 125 μm cladding diameter and ~245 μm diameter outer polymer buffer. The imaging depth is 1-1.5 mm in tissue and somewhat less in our wax sample materials. In air, the OCT beam diverges at an angle of 16 degrees and effective axial resolution is ~8.8 μm. In water or tissue the divergence is ~12 degrees with ~6.6 μm resolution. A sample axial image (A-Mode) with zero reference point located at the tip of the fiber is shown in FIG. 2. By moving the probe laterally, a sample cross section image is generated (B-Mode) as shown in FIG. 8.

The CP-OCT system provided the robot with the distance from the probe to the surface of the sample. Each axial scan was processed by first thresholding to remove baseline noise, and then smoothing with a Savitzky-Golay filter to preserve peak locations, amplitudes and widths. To locate the peaks, a simple zero-crossing of signal derivative was used. The acquisition time and signal processing yields a sampling rate of ~200 Hz with approximate latency of one frame.

Sample Materials:

We developed two artificial phantoms for consistent evaluation in these preliminary experiments. For the safety barrier and surface tracking tasks, we use a composite of three 60 μm thick layers of scotch tape on a dense wooden plank. This provides a strong multi-peak axial scan signal that is analogous to that generated by the multilayered structures of the retina. For the targeting tasks, we needed a phantom with 100-300 μm diameter cavities located near the surface and the ability to display any physical interaction with the sample. Sheet lining wax (McMaster 8691K31) with a low softening point (135° C.) was placed on an aluminum sheet and heated to boiling. Rapid cooling produces many thin-walled bubbles and any physical contact between the pick and sample surface leaves permanent marks visible in OCT.

Experimental Setup:

Our experimental setup is illustrated in FIG. 6. The microsurgical instrument is mounted on an extremely precise Cartesian positioning robot consisting of three orthogonally mounted linear stages. The position resolution is 1 μm and measured repeatability is about ±1 μm for range of motion required for this experiment (<2 mm). This robot was chosen for experimental convenience, and could be replaced in actual practice by a system similar to (Mitchell, B., Koo, J., Iordachita, I., Kazanzides, P., Kapoor, A., Handa, J., Hager, G., Taylor, R.: Development and Application of a New Steady-Hand Manipulator for Retinal Surgery. IEEE ICRA, 623-629 (2007); Riviere, W. Ang, and P. Khosla, "Toward active tremor canceling in handheld microsurgical instruments," IEEE Trans Rob Autom, vol. 19, pp. 793-800, 2003). The robot is interfaced to a PC workstation through a commercial motion controller (Galil DMC 1886). A commercial 6 DOF force-torque sensor (ATI Nano43) is mounted on the robot and also interfaced to the PC as a user interface. Open-source robot control software developed in our laboratory (Kapoor A., Deguet A., Kazanzides P., Software components and frameworks for medical robot control. IEEE ICRA, pp. 3813-3818, 2006) is used to implement cooperative "hands on" control for the robot's motion. The OCT system is implemented on a separate PC and communicates to the robot PC via Ethernet. The test samples are mounted on a separate manually actuated micrometer stage placed beneath the probe. An inspection video microscope (Omano E-ZVU/V15) is positioned to simultaneously image the side view of the sample and probe at 90× magnification (not shown).

Methods

We have demonstrated our system in the context of three sample tasks: enforcement of safety barriers, "tracking" to maintain a constant distance from a surface, and accurate placement of the probe on targets identified in a scanned OCT image. Relatively low velocities were chosen based on surgical preference when operating close to the retina and the limited movement in the eye during surgery due to constraints by insertion of tools through the sclera and effects of anesthetics.

In the safety barrier task, the system enforced a safety constraint to prevent the probe from approaching the target surface closer than a specified threshold distance. The robot moved freely within the 1D workspace to comply with forces exerted by the user on the control handle, with the exception of the forbidden boundary sensed via the OCT. This "virtual wall" was reached when the tip of the probe was located ~150 μm from the sample surface. A bare optical fiber was used as a probe. Five trials were performed with different robot velocity limits: 100, 200, 300, 400, 500 μm/sec.

In the surface tracking task, the sample surface was moved up and down with the manual micrometer stage while the robot was controlled to maintain a constant OCT-reported distance of 150 μm from the sample surface. One intention for the surface tracking was to correct for retinal motion due to respiratory function, hence we chose the sinusoidal frequency to be around 0.2 Hz and magnitude that encompasses expected ranges of retinal motion.

In the targeting task, the robot was instructed to scan the pick in 2 μm increments laterally across the sample surface. The A-mode images from the OCT system were then combined to make a B-mode image. The evolving B-mode image was displayed continuously to the user, who could use a mouse at any time to click on a target within the image. The robot would then interrupt its scan, move back to a position over the identified target, and then slowly insert the pick tip to the depth of the designated target, based on depth feedback provided by the OCT system. The probe was then withdrawn and a second B-mode scan was taken to observe the created defect in the sample surface.

Results

Figure 7:
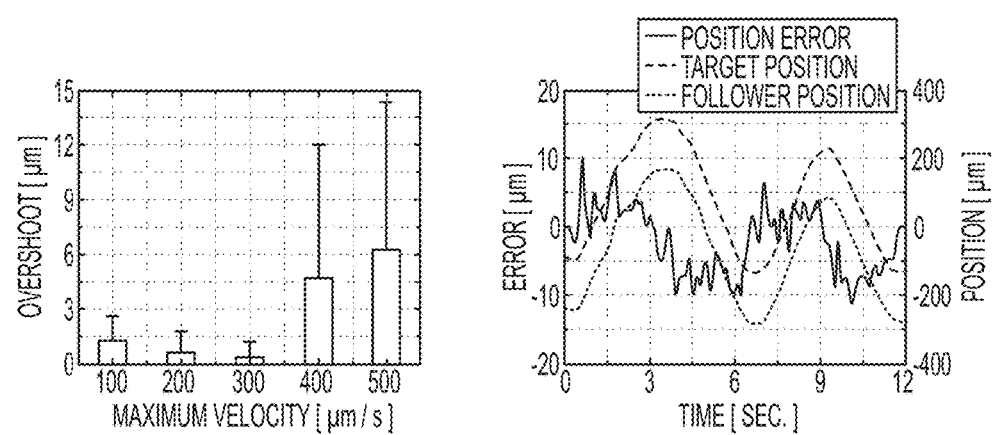
FIG. 7 provides performance data for a surgical system according to an embodiment of the current invention configured with a safety barrier (left); and overshoot error vs. maximum allowable velocity, surface tracking with 150 µm standoff (right).

The results for the safety barrier task are shown in FIG. 7 (left). The observed overshoot into the "unsafe" zone was negligible for robot speeds up to ~300 μm/sec and still quite modest up to ~500 μm/sec, using only a very naïve control method. Further improvements are expected with our next generation OCT system (which has higher sample rate) and with refinements in the robot design and control.

The results of dynamic response when tracking sinusoidal surface motion are shown in FIG. 7 (right). We were able to keep the tool tip within about 10 μm of the desired 150 μm standoff from the target surface while the surface moved at about 200 μm/sec.

The results of the targeting task are illustrated in FIG. 8. The top B-Scan shows a subsurface bubble with 30-50 μm membrane and the user specified incision location. The bottom shows the post-intervention B-Scan with an overlay depicting approximate orientation and location of the instrument tip at the target. The defect clearly resembles the geometry of the tip, as well as good alignment with planned incision position.

Discussion and Alternative Embodiments

"Smart" instruments combining real time sensing with tissue manipulation have significant potential to improve surgical practice, especially when combined with real time visualization, robotic devices, and computer-based decision support. In this work, we have introduced a new class of microsurgical instruments for retinal surgery, incorporating fiber-optic common path Fourier domain OCT sensing.

We have found that very small instruments (~0.5 mm diameter) incorporating fiber-optic OCT can be constructed and used to identify tissue boundaries beyond the tip of the instruments. Further, the instrument can be scanned laterally to construct 2D and 3D images from the single A-mode images produced by the basic sensor. We have demonstrated that the sensor can provide real time feedback on the distance from the tool tip to a surface and can be used to enforce safety barriers or support surface following with a robot. Finally, we have shown that these capabilities can be combined to enable user identification of a subsurface target in a scanned image followed by automated placement of the instrument tip on the target. All of these capabilities can be very useful in clinical vitreoretinal systems according to some embodiments of the current invention.

The current experiments were performed with the probe perpendicular to the sample surface. Although OCT can identify layers while looking obliquely into tissue at the angles that will be encountered in retinal surgery, it is still necessary to account for approach angle to get correct range data. Approaches to address this can include robot pose feedback and tracking of tools in the stereo video microscope. Practical issues that may be address in further embodiments of the current invention include: fabrication processes, optical path occlusion by stray particles in the microenvironment, improvement in the speed of OCT data acquisition, and interfacing to our surgical robots.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A surgical system, comprising:
   a surgical instrument, comprising:
      a surgical tool having a proximal end and a distal end, the surgical tool being adapted to mechanically manipulate tissue, and
      an optical sensor having at least a portion attached to said surgical tool, the optical sensor having a field of view;
   a data processor in communication with said optical sensor so as to receive information from said optical sensor; and
   an information output system in communication with said data processor and arranged to display information to a surgeon during a surgical procedure,
   wherein said surgical tool includes a reference portion,
   wherein said optical sensor has an end fixed relative to said reference portion of said surgical tool, said reference portion being within the field of view of the optical sensor such that said reference portion of said surgical tool can be detected along with tissue that is proximate or in contact with said distal end of said surgical tool while in use, and
   wherein the data processor provides information regarding a relative distance of said distal end of said surgical tool to selected portions of said tissue based on detected light reflected back from both said reference portion of said surgical tool and said tissue.

2. A surgical system according to claim 1, wherein said optical sensor comprises a visual imaging system.

3. A surgical system according to claim 2, wherein said visual imaging system comprises an optical fiber, said visual imaging system being configured to simultaneously image said reference portion of said surgical tool and said tissue proximate or in contact with said distal end of said surgical tool.

4. A surgical system according to claim 1, wherein said optical sensor comprises an optical coherence tomography system.

5. A surgical system according to claim 4, wherein said optical coherence tomography system comprises an optical fiber that provides said fixed end of said optical sensor, said optical fiber being arranged to direct light to both said reference portion of said surgical tool and said tissue proximate or in contact with said distal end of said surgical tool and to detect light reflected back from both said reference portion of said surgical tool and said tissue to provide information regarding a relative distance of said distal end of said surgical tool to selected portions of said tissue.

6. A surgical system according to claim 5, wherein said surgical tool is a pick that is suitable for use in eye surgery.

7. A surgical system according to claim 5, wherein said surgical tool is at least one of a pick, tweezers, a knife, scissors, an injector, a fragmenter, a spatula, a peeling tool, or a vitrectomy tool.

8. A surgical system according to claim 1, further comprising a robotic system, wherein said surgical tool is attached to said robotic system.

9. A surgical system according to claim 8, wherein said robotic system is a hand-held robotic system.

10. A surgical system according to claim 8, wherein said robotic system is a steady-hand robotic system.

11. A surgical system according to claim 8, wherein said data processor is configured to provide a feedback response signal to said robotic system based on a value of at least one of a relative distance of said distal end of said surgical instrument from said tissue or a position of said instrument such that said robotic system provides a feedback response.

12. A surgical system according to claim 1, wherein said data processor is configured to provide at least one of a warning signal or a feedback response signal based on a value of a relative position of said distal end of said surgical instrument to said tissue.

13. A surgical system according to claim 1, wherein the data processor is configured to:
   provide a first signal corresponding to a first light reflection from said reference portion and a second signal corresponding to a second light reflection from said tissue; and provide relative distance information between the distal end of the surgical tool and said tissue based on said first and second signals.

14. A surgical system according to claim 1, wherein said reference portion comprises said distal end of the surgical tool.

15. A surgical instrument, comprising:
a surgical tool having a proximal end and a distal end, the surgical tool being adapted to mechanically manipulate tissue; and
an optical sensor that is configured to provide information to a data processor, the optical sensor having at least a portion attached to said surgical tool, and the optical sensor having a field of view,
wherein said surgical tool includes a reference portion,
wherein said optical sensor has an end fixed relative to said reference portion, said reference portion being within the field of view of the optical sensor such that said reference portion of said surgical tool can be detected along with tissue that is proximate or in contact with said distal end of said surgical tool while in use, and
wherein the data processor provides information regarding a relative distance of said distal end of said surgical tool to selected portions of said tissue based on detected light reflected back from both said reference portion of said surgical tool and said tissue.

16. A surgical instrument according to claim 15, wherein said optical sensor comprises a visual imaging system.

17. A surgical instrument according to claim 16, wherein said visual imaging system comprises an optical fiber, said visual imaging system being configured to simultaneously image said reference portion of said surgical tool and said tissue proximate or in contact with said distal end of said surgical tool.

18. A surgical instrument according to claim 15, wherein said optical sensor comprises an optical coherence tomography system.

19. A surgical instrument according to claim 18, wherein said optical coherence tomography system comprises an optical fiber that provides said fixed end of said optical sensor, said optical fiber being arranged to direct light to both said reference portion of said surgical tool and said tissue proximate or in contact with said distal end of said surgical tool and to detect light reflected back from both said reference portion of said surgical tool and said tissue to provide information regarding a relative distance of said distal end of said surgical tool to selected portions of said tissue.

20. A surgical instrument according to claim 19, wherein said surgical tool is a pick that is suitable for use in eye surgery.

21. A surgical instrument according to claim 19, wherein said surgical tool is at least one of a pick, tweezers, a knife, scissors, an injector, a fragmenter, a spatula, a peeling tool, or a vitrectomy tool.

22. A surgical instrument according to claim 15, wherein said surgical tool is adapted to be at least one of held by a surgeon for performing manual surgery or to be attached to a robotic system for at least one of robotic or robot-assisted surgery.

* * * * *

UNITED STATES PATENT AND TRADEMARK OFFICE
CERTIFICATE OF CORRECTION

PATENT NO. : 10,045,882 B2
APPLICATION NO. : 12/917168
DATED : August 14, 2018
INVENTOR(S) : Balicki et al.

Page 1 of 1

It is certified that error appears in the above-identified patent and that said Letters Patent is hereby corrected as shown below:

In the Specification

Column 1, Lines 10-13:
"This invention was made with government support number 1R01 EB 007969-01 awarded by the Department of Health and Human Services, National Institutes of Health. The government has certain rights in the invention." should read --This invention was made with government support under EB007969 awarded by the National Institutes of Health and EEC9731478 awarded by the National Science Foundation. The government has certain rights in the invention.--

Signed and Sealed this
Twenty-fifth Day of August, 2020

Andrei Iancu
*Director of the United States Patent and Trademark Office*